US006353022B1

(12) United States Patent
Schneider et al.

(10) Patent No.: US 6,353,022 B1
(45) Date of Patent: Mar. 5, 2002

(54) COMPOSITIONS CONTAINING HYDROXYEICOSATETRAENOIC ACID DERIVATIVES AND METHODS OF USE IN TREATING DRY EYE DISORDERS

(75) Inventors: L. Wayne Schneider, Crowley; Daniel A. Gamache, Arlington; Lori K. Weimer, The Woodlands; Timothy L. Kessler, Dallas; Zhongyou Wei, Fort Worth; Terri Pasquine, Arlington; John M. Yanni, Burleson; Haresh G. Bhagat, Fort Worth, all of TX (US)

(73) Assignee: Alcon Universal Ltd., Hunenberg (CH)

( * ) Notice: Subject to any disclaimer, the term of this patent is extended or adjusted under 35 U.S.C. 154(b) by 0 days.

(21) Appl. No.: 09/694,796

(22) Filed: Oct. 23, 2000

Related U.S. Application Data (60) Provisional application No. 60/164,385, filed on Nov. 9, 1999, provisional application No. 60/164,384, filed on Nov. 9, 1999, and provisional application No. 60/164,370, filed on Nov. 9, 1999.

(51) Int. Cl.$^7$ ...................... A61K 31/215; A61K 31/557
(52) U.S. Cl. ...................... 514/530; 514/573; 514/75; 514/76
(58) Field of Search ................ 514/530, 573, 514/76, 75, 912

(56) References Cited

U.S. PATENT DOCUMENTS

| | | | |
|---|---|---|---|
| 3,991,759 A | 11/1976 | Urquhart | 128/260 |
| 4,131,651 A | 12/1978 | Shah et al. | 424/78 |
| 4,370,325 A | 1/1983 | Packman | 424/245 |
| 4,409,205 A | 10/1983 | Shively | 424/78 |
| 4,421,748 A | 12/1983 | Trager et al. | 424/199 |
| 4,744,980 A | 5/1988 | Holly | 424/78 |
| 4,753,945 A | 6/1988 | Gilbard et al. | 514/263 |
| 4,818,537 A | 4/1989 | Guo | 424/427 |
| 4,868,154 A | 9/1989 | Gilbard et al. | 514/154 |
| 4,883,658 A | 11/1989 | Holly | 424/80 |
| 4,906,467 A | 3/1990 | Schwartzman et al. | 424/80 |
| 4,914,088 A | 4/1990 | Glonek et al. | 514/76 |
| 4,921,644 A | 5/1990 | Lau et al. | 264/4.1 |
| 4,923,700 A | 5/1990 | Kaufman | 424/427 |
| 4,966,773 A | 10/1990 | Gressel et al. | 424/489 |
| 5,041,434 A | 8/1991 | Lubkin | 514/182 |
| 5,064,655 A | 11/1991 | Uster et al. | 424/450 |
| 5,075,104 A | 12/1991 | Gressel et al. | 424/78.04 |
| 5,174,988 A | 12/1992 | Mautone et al. | 424/45 |
| 5,278,151 A | 1/1994 | Korb et al. | 514/76 |
| 5,290,572 A | 3/1994 | MacKeen | 424/602 |
| 5,294,607 A | 3/1994 | Glonek et al. | 514/76 |
| 5,306,483 A | 4/1994 | Mautone | 424/45 |
| 5,358,706 A | 10/1994 | Marlin et al. | 424/78.04 |
| 5,371,108 A | 12/1994 | Korb et al. | 514/762 |
| 5,389,383 A | 2/1995 | Huth | 424/650 |
| 5,403,598 A | 4/1995 | Beck et al. | 424/717 |
| 5,403,841 A | 4/1995 | Lang et al. | 514/226.8 |
| 5,455,265 A | 10/1995 | Chandraratna | 514/448 |
| 5,578,586 A | 11/1996 | Glonek et al. | 514/76 |
| 5,620,921 A | 4/1997 | Sullivan | 514/178 |
| 5,696,166 A | 12/1997 | Yanni et al. | 514/573 |
| 5,800,807 A | 9/1998 | Hu et al. | 424/78.04 |

FOREIGN PATENT DOCUMENTS

| | | |
|---|---|---|
| CA | 1 251 736 | 3/1989 |
| EP | 0 097 059 A2 | 12/1983 |
| EP | 0 132 089 A1 | 1/1985 |
| WO | WO 91/12808 | 9/1991 |
| WO | WO 92/04905 | 4/1992 |

OTHER PUBLICATIONS

Alpert et al., "Human Tracheal Epithelial Cells Selectively Incorporate 15–Hydroxyeicosatetraenoic Acid into Phosphatidylinositol," *Am. J. Respir. Cell Mol. Biol.*, vol. 8, pp. 273–281 (1993).

Corey et al., 12–Hydroxy–5.8.15–(Z)–10–(E)–Eicosatetraenoic Acid (12–HETE). *The Logic of Chemical Synthesis*, John Wiley and Sons, sections 12.9 and 12.11 (1989).

Corfield et al., "Ocular Mucins: Purification, Metabolism and Functions," *Prog Retinal Eye Res.*, vol. 16, pp. 627–656 (1997).

Danjo et al., "Alternation of Mucin in Human Conjunctival Epithelia in Dry Eye," *Invest Ophthalmol Vis. Sci.*, vol. 39; pp. 2602–2609 (1998).

Dartt et. al., Vasoactive intestinal peptide–stimulated glycoconjugate secretion from conjunctival goblet cells. Experimental Eye Research, vol. 63, pp. 27–34, (1996).

Dilly et al., "Surface Changes in the Anesthetic Conjunctiva in Man, with Special Reference to the Production of Mucus from a Non–Goblet–Cell Source," *British Journal of Ophthalmology*, vol. 65; pp. 833–842 (1981).

Dohlman, "Symposium on the Dry Eye, New Concepts in Ocular Xerosis," *Ophthalmological Societies of the United Kingdom*, vol. XCI; pp. 105–118 (1971).

Glasgow et al., "Tear lipocalins bind a broad array of lipid ligands,"*Current Eye Research*, vol. 14(5), pp. 363–372 (1995).

Graber et al., 15–Hydroxyeicosatetraenoic Acid Stimulates Migration of Human Retinal Microvessel Endothelium In Vitro and Neovascularization In Vivo, *Prostaglandins*, vol. 39 (6); pp. 665–673 (1990).

Graff et al., Activation of Soluble Splenic Cell Guanylate Cyclase by Prostaglandin Endoperoxides, and Fatty Acid Hydroperoxides, *J. of Bilogical Chemistry*, vol. 253 (21) pp. 7662–7676 (1978).

Graff et al., "Preparation of 15–L–Hydroperoxy–5.8.11.13–eicosatetraenoic Acid 9215 (HPETE)," *Methods in Enzymology*, vol. 86; pp. 386–392 (1982).

(List continued on next page.)

*Primary Examiner*—Zohreh Fay
(74) *Attorney, Agent, or Firm*—Patrick M. Ryan (57) ABSTRACT

Compositions containing one or more HETE derivative(s) and an effective concentration of ethanol and methods of use for treating dry eye are disclosed.

22 Claims, 2 Drawing Sheets

OTHER PUBLICATIONS

Greiner et al., "Histochemical Analysis of Secretory Vesicles in Non–Goblet Conjunctival Epithelial Cells," *Acta Ophthalmol.*, vol. 63; pp. 89–92 (1985).

Greiner et al., Meibomian gland phospholipids, *Current Eye Research*, vol. 15(4); pp. 371–375 (1996).

Greiner et al., "Mucus Secretory Vesicles in Conjunctival Epithelial Cells of Wearers of Contact Lenses," *Arch Ophthalmol.*, vol. 98; pp. 1843–1846 (1980).

Greiner et al., "Phospholipids in Meibomian Gland Secretion," *Ophthalmic Res.*, vol. 28, pp. 44–49 (1996).

Hamberg et al., "Identification of 15–hydroxy–5.8.11.13–eicosatetraenoic acid (15–HETE) as a major metabolite of arachidonic acid in human lung, "*Acta Physiol Scand.*, vol. 110; pp. 219–221 (1980).

Holly et al., "Tear Physiology and Dry Eyes," *Surv. Ophthalmol.*, vol. 22; pp. 69–87 (1977).

Holzfeind et al., "The Human Lacrimal Gland Synthesizes Apolipoprotein D mRNA in Addition to Tear Prealbumin mRNA, Both Species Encoding Members of the Lipocalin Superfamily," *Exp. Eye Res.*, vol. 65, pp. 495–500 (1995).

Hutchinson, "Arachidonate 15–lipoxygenase; characteristics and potential biological significance," *Eicosanoids*, vol. 4, pp. 65–74 (1991).

Inatomi et al., "Human Corneal and Conjunctival Epithelia Express MUC1 Mucin," *Invest Ophthalmol Vis Sci.*, vol. 36; pp. 1818–1827 (1995).

Jansen et al., "Phospholipids Chiral at Phosphorus. Synthesis and Stereospecificity of Phosphorothioate Analogues of Platelet–Activating Factor," *Biochemistry*, vol. 27, pp. 4619–4624 (1988).

Johnson et al., 15–Hydroxyeicosatetraenoic Acid is a Potent Inflammatory Mediator and Agonist of Canine Tracheal Mucus Secretion, from the Hypersensitivity Diseases Research, Lipids Research. The Upjohn Company, Kalamazoo, Michigan, pp. 917–922 (1984).

Kessing et al., "Mucous Gland System of the Conjunctiva," *Acta Ophthalmol. Suppl.*, vol. 95; pp. 1–133 (1968).

Korb et al., Tear Film Lipid Layer Formation: Implications for Contact Lens Wear, *Optometry and Vision Science*, vol. 73(3), pp. 189–192 (1996).

Legrand et al., "Substitution of 15–Hydroxyeicosatetraenoic Acid in the Phosphoinositide Signaling Pathway," *J. of Biological Chemistry*, vol. 266 (12), pp. 7570–7577 (1991).

Lemp et al., "Report of the National Eye Institute/Industry Workshop on Clinical Trials in Dry Eyes," *CLAO*, vol. 21(4), pp. 221–231 (1995).

Lemp, "Tear Substitutes in the Treatment of Dry Eyes," *External Ocular Diseases: Diagnosis and Current Therapy*, Laibson and Trobe (ed.) Little, Brown and Company, Boston; vol. 13(4); pp. 145–153 (1973).

Marom et al., "Effects of Arachidonic Acid, Monohydroxyeicosatetraenoic Acid and Prostaglandins on the Release of Mucous Glycoproteins from Human Airways In Vitro," *The J. of Clinical Investigation*, vol. 67; pp. 1695–1702 (1981).

Marom et al., "Human Airway Monohydroxyeicosatetraenoic Acid Generation and Mucus Release," *Journal of Clinical Investigation*, vol. 72, pp. 122–127 (1983).

Masferrer et al., "12(R)–Hydroxyeicosatetraenoic Acid, An Endogenous corneal Arachidonate Metabolite, Lowers Intraocular Pressure in Rabbits," *Investigative Ophthalmology and Visual Science*, vol. 31(3); pp. 535–539 (1990).

McCulley et al., "Tear Film Structure and Dry Eye," *Contactologia*, vol. 20, pp. 145–149 (1998).

Mysore et al., "Controlled Ocular Drug Delivery and Vesicular Systems: An Overview," *Indian Drugs*, vol. 33(9), pp. 431–442 (1996).

Nakamura et. al., "Gefarnate stimulates secretion of mucin-–like glycoproteins by corneal epithelium in vitro and protects corneal epithelium from dessication in vivo," *Experimental Eye Research*, vol. 65, pp. 569–574 (1997).

Ohno, M.; Otsuka, M. Organic Reactions, vol. 37, p. 1 (1989).

Ohyama et al., "Sensitive Densitometry for the Determination of Platelet–activating Factor and Other Phospholipids in Human Tears," *Analyst*, vol. 121, pp. 1943–1947 (1996).

Pleyer et al., "Analysis of Interactions Between the Corneal Epithelium and Liposomes" Qualitative and Quantitative Fluorescence Studies of a Corneal Epithelial Cell Line, *Survey of Ophthalmology.*, vol. 39 (Supl. 1), S3–S16 (1995).

Profita et al., "Interleukin–4 Enhances 15–Lipoxygenase Activity and Incorporation of 15(S)–HETE into Cellular Phospholipids in Cultured Pulmonary Epithelial Cells," *Am. J. Respir. Cell Mol. Biol.*, vol. 20, pp. 61–68 (1999).

Prydal et al., "Study of Human Tear Film Thickness and Structure Using Laser Interferometry," *Invest Ophthalmol Vis Sci.*, vol. 33; pp. 2006–2011 (1992).

Shelhamer et al., "The Effects of Arachinoids and Leukotrienes on the Release of Mucus from Human Airways," *Chest Supplement*, $24^{th}$ Aspen Lung Conference, vol. 81(5); pp. 36S–37S (1982).

Shigemitsu et al., "Effects of Mucin Ophthalmic Solution on Epithelial Wound Healing in Rabbit Cornea," *Ophthalmic Res.*, vol. 29; pp. 61–66 (1997).

Shine et al., Keratoconjunctivitis Sicca Associated with Meibomian Secretion Polar Lipid Abnormality, *Arch. Ophthalmology*, vol. 116, pp. 849–852 (1998).

Watanabe et al., "Human Corneal and Conjunctival Epithelia Produce a Mucin–like Glycoprotein for the Apical Surface," *Invest Ophthalmol Vis Sci.*, vol. 36; pp. 337–344 (1995).

Wiggins et al., "12(S)–Hydroxy–5,8.10.14–Eicosatetraenoic Acid is a More Potent Neutrophil Chemoattractant Than the 12(R) Epimer in the Rat Cornea," *Prostaglandins*, vol. 49(2) pp. 131–141 (1990).

Yanni et al., "Effect of Intravenously Administered Lipoxygenase Metabolites on Rat Tracheal Mucous Gel Layer Thickness," *Int Arch Allergy Appl Immunol*, vol. 90 pp. 307–309 (1989).

Yu et al., "Effect of Polar Head Groups on the Interactions of Phospholipase $A_2$ with Phosphonate Transition–State Analogues," *Biochemistry*, vol. 32, pp. 10185–10192 (1993).

Zhang et al., "Enzymatic Asymmetric Hydroxylation of Pentadienols Using Soybean Lipoxygenase," *J. Am. Chem. Soc.*, vol. 111(26), pp. 9241–9242 (1989).

Zhu et al., Synthesis of Phospholipids Bearing a Conjugated Oxo–polyunsaturated Fatty Acid Residue, *J. Chem. Research* (S)., vol. 8, pp. 500–501 (1999).

COMPOSITIONS CONTAINING HYDROXYEICOSATETRAENOIC ACID DERIVATIVES AND METHODS OF USE IN TREATING DRY EYE DISORDERS

This application claims priority to co-pending U.S. Provisional Applications, U.S. Serial No. 60/164,385 filed Nov. 9, 1999; U.S. Serial No. 60/164,384 filed Nov. 9, 1999, and U.S. Serial No. 60/164,370 filed Nov. 9, 1999.

The present invention is directed to improved compositions containing hydroxyeicosatetraenoic acid derivatives and ethanol and methods for their use in treating dry eye.

BACKGROUND OF THE INVENTION

Dry eye, also known generically as keratoconjunctivitis sicca, is a common ophthalmological disorder affecting millions of Americans each year. The condition is particularly widespread among post-menopausal women due to hormonal changes following the cessation of fertility. Dry eye may afflict an individual with varying severity. In mild cases, a patient may experience burning, a feeling of dryness, and persistent irritation such as is often caused by small bodies lodging between the eye lid and the eye surface. In severe cases, vision may be substantially impaired. Other diseases, such as Sjogren's disease and cicatricial pemphigoid manifest dry eye complications.

Although it appears that dry eye may result from a number of unrelated pathogenic causes, all presentations of the complication share a common effect, that is the breakdown of the pre-ocular tear film, which results in dehydration of the exposed outer surface and many of the symptoms outlined above (Lemp, Report of the National Eye Institute/Industry Workshop on Clinical Trials in Dry Eyes, *The CLAO Journal*, volume 21, number 4, pages 221–231 (1995)).

Practitioners have taken several approaches to the treatment of dry eye. One common approach has been to supplement and stabilize the ocular tear film using so-called artificial tears instilled throughout the day. Other approaches include the use of ocular inserts that provide a tear substitute or stimulation of endogenous tear production.

Examples of the tear substitution approach include the use of buffered, isotonic saline solutions containing water soluble polymers that render the solutions more viscous and thus less easily shed by the eye. Tear reconstitution is also attempted by providing one or more components of the tear film such as phospholipids and oils. Phospholipid compositions have been shown to be useful in treating dry eye; see, e.g., McCulley and Shine, Tear film structure and dry eye, *Contactologia*, volume 20(4), pages 145–49 (1998); and Shine and McCulley, Keratoconjunctivitis sicca associated with meibomian secretion polar lipid abnormality, *Archives of Ophthalmology*, volume 116(7), pages 849–52 (1998). Examples of phospholipid compositions for the treatment of dry eye are disclosed in U.S. Pat. No. 4,131,651 (Shah et al.), U.S. Pat. No. 4,370,325 (Packman), U.S. Pat. No. 4,409,205 (Shively), U.S. Pat. Nos. 4,744,980 and 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.) and U.S. Pat. No. 5,578,586 (Glonek et al.). U.S. Pat. No. 5,174,988 (Mautone et al.) discloses phospholipid drug delivery systems involving phospholipids, propellants and an active substance.

U.S. Pat. No. 3,991,759 (Urquhart) discloses the use of ocular inserts in the treatment of dry eye. Other semi-solid therapy has included the administration of carrageenans (U.S. Pat. No. 5,403,841, Lang) which gel upon contact with naturally occurring tear film.

Another approach involves the provision of lubricating substances in lieu of artificial tears. For example, U.S. Pat. No. 4,818,537 (Guo) discloses the use of a lubricating, liposome-based composition, and U.S. Pat. No. 5,800,807 (Hu et al.) discloses compositions containing glycerin and propylene glycol for treating dry eye.

Aside from the above efforts, which are directed primarily to the alleviation of symptoms associated with dry eye, methods and compositions directed to treatment of the dry eye condition have also been pursued. For example, U.S. Pat. No. 5,041,434 (Lubkin) discloses the use of sex steroids, such as conjugated estrogens, to treat dry eye condition in post-menopausal women; U.S. Pat. No. 5,290,572 (MacKeen) discloses the use of finely divided calcium ion compositions to stimulate pre-ocular tear film production; and U.S. Pat. No. 4,966,773 (Gressel et al.) discloses the use of microfine particles of one or more retinoids for ocular tissue normalization.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive. Transient symptoms of dry eye associated with refractive surgery have been reported to last in some cases from six weeks to six months or more following surgery.

The use of ocular inserts is also problematic. Aside from cost, they are often unwieldy and uncomfortable. Further, as foreign bodies introduced in the eye, they can be a source of contamination leading to infections. In situations where the insert does not itself produce and deliver a tear film, artificial tears must still be delivered on a regular and frequent basis.

In view of the foregoing, there is a clear need for an effective, convenient treatment for dry eye that is capable of alleviating symptoms, as well as treating the underlying physical and physiological deficiencies of dry eye.

Mucins are proteins which are heavily glycosylated with glucosamine-based moieties. Mucins provide protective and lubricating effects to epithelial cells, especially those of mucosal membranes. Mucins have been shown to be secreted by vesicles and discharged on the surface of the conjunctival epithelium of human eyes (Greiner et al., Mucous Secretory Vesicles in Conjunctival Epithelial Cells of Wearers of Contact Lenses, *Archives of Ophthahnology*, volume 98, pages 1843–1846 (1980); and Dilly et al., Surface Changes in the Anaesthetic Conjunctiva in Man, with Special Reference to the Production of Mucous from a Non-Goblet-Cell Source, *British Journal of Ophthalmology*, volume 65, pages 833–842 (1981)). A number of human-derived mucins which reside in the apical and subapical corneal epithelium have been discovered and cloned (Watanabe et al., Human Corneal and Conjunctival Epithelia Produce a Mucin-Like Glycoprotein for the Apical Surface, *Investigative Ophthalmology and Visual Science*, volume 36, number 2, pages 337–344 (1995)). Recently, Watanabe discovered a new mucin which is secreted via the cornea apical and subapical cells as well as the conjunctival epithelium of the human eye (Watanabe et al., *IOVS*, volume 36, number 2, pages 337–344 (1995)). These mucins provide lubrication, and additionally attract and hold moisture and sebaceous material for lubrication and the corneal refraction of light.

Mucins are also produced and secreted in other parts of the body including lung airway passages, and more specifically from goblet cells interspersed among tracheal/bronchial epithelial cells. Certain arachidonic acid metabolites have been shown to stimulate mucin production in these cells. Yanni reported the increased secretion of mucosal glycoproteins in rat lung by hydroxyeicosatetraenoic acid to ("HETE") derivatives (Yanni et al, Effect of Intravenously Administered Lipoxygenase Metabolites on Rat Trachael Mucous Gel Layer Thickness, *International Archives of Allergy And Applied Immunology*, volume 90, pages 307–309 (1989)). Similarly, Marom has reported the production of mucosal glycoproteins in human lung by HETE derivatives (Marom et al., Human Airway Monohydroxyeicosatetraenoic Acid Generation and Mucous Release, *Journal of Clinical Investigation*, volume 72, pages 122–127 (1983)).

Agents claimed for increasing ocular mucin and/or tear production include vasoactive intestinal polypeptide (Dartt et. al., Vasoactive intestinal peptide-stimulated glycoconjugate secretion from conjunctival goblet cell, *Experimental Eye Research*, volume 63, pages 27–34, (1996)), gefarnate (Nakmura et. al., Gefarnate stimulates secretion of mucin-like glycoproteins by corneal epithelium in vitro and protects corneal epithelium from dessication in vivo, *Experimental Eye Research*, volume 65, pages 569–574 (1997)), liposomes (U.S. Pat. No. 4,818,537), androgens (U.S. Pat. No. 5,620,921), melanocycte stimulating hormones (U.S. Pat. No. 4,868,154), phosphodiesterase inhibitors (U.S. Pat. No. 4,753,945), and retinoids (U.S. Pat. No. 5,455,265). However, many of these compounds or treatments suffer from a lack of specificity, efficacy and potency and none of these agents have been marketed so far as therapeutically useful products to treat dry eye and related ocular surface diseases.

U.S. Pat. No. 5,696,166 (Yanni et al.) discloses compositions containing HETEs and met hods of use for treating dry eye. Yanni et al. discovered that compositions comprising HETEs increase ocular mucin secretion when administered to a patient and are thus useful in treating dry eye. The inventors of the present invention have improved on such compositions and methods by inventing HETE derivative compositions having improved efficacy relative to those disclosed in the U.S. Pat. No. 5,696,166 patent.

SUMMARY OF THE INVENTION

The present invention is directed to compositions and methods for the treatment of dry eye and other disorders requiring the wetting of the eye, including symptoms of dry eye associated with refractive surgery such as LASIK surgery. More specifically, the present invention discloses improved compositions containing HETE derivatives and methods for treating dry eye-type diseases and disorders. The HETE containing compositions comprise one or more HETE derivatives and an effective concentration of ethanol to improve the efficacy of the HETE derivative(s) in vivo.

The compositions are preferably administered topically to the eye.

In a preferred embodiment, HETE derivatives are formulated with an artificial tear component or phospholipid in order to provide compositions that give both immediate and long term relief from dry eye or other disorders requiring the wetting of the eye.

DETAILED DESCRIPTION OF THE INVENTION

It has now been discovered that HETE derivative-containing compositions comprising an effective amount of ethanol are more efficacious for treating dry eye-type disorders than corresponding compositions containing no ethanol. As used herein, the term "HETE derivative" refers to any hydroxyeicosatetraenoic acid-like derivative that stimulates ocular mucin production and/or secretion following topical ocular application, and are of the following formulas (I), (II) or (III):

wherein:

X is OR or NHR;

R is H, substituted or unsubstituted alkyl, cycloalkyl, (cycloalkyl)alkyl, aryl, arylalkyl, wherein the substitution is made with a moiety selected from the group consisting of: alkyl, halogen, hydroxy and functionally modified hydroxy; and Y is where in R" is H or OR" is a functionally modified hydroxy group.

Included within the scope of the present invention are the individual enantiomers of the compounds of the present invention, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (*Asymmetric Synthesis*; J. D. Morrison and J. W. Scott, Eds.; Academic Press Publishers: New York, 1983–1985, volumes 1–5; *Principles of Asymmetric Synthesis*; R. E. Gawley and J. Aube, Eds.; Elsevier Publishers: Amsterdam, 1996). They may also be isolated from racemic and non-racemic mixtures by a number of known methods, e.g. by purification of a sample by chiral HPLC (*A Practical Guide to Chiral Separations by HPLC*; G. Subramanian, Ed.; VCH Publishers: New York, 1994; *Chiral Separations by HPLC*; A. M. Krstulovic, Ed.; Ellis Horwood Ltd. Publishers, 1989), or by enantioselective hydrolysis of a carboxylic acid ester sample by an enzyme (Ohno, M.; Otsuka, M. *Organic Reactions*, volume 37, page 1 (1989)). Those skilled in the art will appreciate that racemic and non-racemic mixtures may be obtained by several means, including without limitation, nonenantioselective synthesis, partial resolution, or even mixing samples having different enantiomeric ratios. Departures may be made from such details within the scope of the accompanying claims without departing from the principles of the invention and without sacrificing its advantages. Also included within the scope of the present invention are the individual isomers substantially free of their respective enantiomers.

The term "free hydroxy group" means an OH. The term "functionally modified hydroxy group" means an OH which has been functionalized to form: an ether, in which an alkyl, aryl, cycloalkyl, heterocycloalkyl, alkenyl, cycloalkenyl, heterocycloalkenyl, alkynyl, or heteroaryl group is substituted for the hydrogen; an ester, in which an acyl group is substituted for the hydrogen; a carbamate, in which an aminocarbonyl group is substituted for the hydrogen; or a carbonate, in which an aryloxy-, heteroaryloxy-, alkoxy-, cycloalkoxy-, heterocycloalkoxy-, alkenyloxy-, cycloalkenyloxy-, heterocycloalkenyloxy-, or alkynyloxy-carbonyl group is substituted for the hydrogen. Preferred moieties include OH, $OCH_2C(O)CH_3$, $OCH_2C(O)C_2H_5$, $OCH_3$, $OCH_2CH_3$, $OC(O)CH_3$, and $OC(O)C_2H_5$.

The term "acyl" represents a group that is linked by a carbon atom that has a double bond to an oxygen atom and a single bond to another carbon atom.

The term "alkyl" includes straight or branched chain aliphatic hydrocarbon groups that are saturated and have 1 to 15 carbon atoms. The alkyl groups may be substituted with other groups, such as halogen, hydroxyl or alkoxy. Preferred straight or branched alkyl groups include methyl, ethyl, propyl, isopropyl, butyl and t-butyl.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl, alkoxy, or lower alkyl. Preferred cycloalkyl groups include cyclopropyl, cyclobutyl, cyclopentyl and cyclohexyl.

The term "alkenyl" includes straight or branched chain hydrocarbon groups having 1 to 15 carbon atoms with at least one carbon-carbon double bond. The chain hydrogens may be substituted with other groups, such as halogen. Preferred straight or branched alkenyl groups include, allyl, 1-butenyl, 1-methyl-2-propenyl and 4-pentenyl.

The term "cycloalkenyl" includes straight or branched chain, saturated or unsaturated aliphatic hydrocarbon groups which connect to form one or more non-aromatic rings containing a carbon-carbon double bond, which can be fused or isolated. The rings may be substituted with other groups, such as halogen, hydroxyl, alkoxy, or lower alkyl. Preferred cycloalkenyl groups include cyclopentenyl and cyclohexenyl.

The term "alkoxy" represents an alkyl group attached through an oxygen linkage.

The term "carbonyl group" represents a carbon atom double bonded to an oxygen atom, wherein the carbon atom has two free valencies.

The term "alkoxycarbonyl" represents an alkoxy group bonded from its oxygen atom to the carbon of a carbonyl group, the carbonyl group itself being bonded to another atom through its carbon atom.

The term "aminocarbonyl" represents an amino group bonded from its nitrogen atom to the carbon atom of a carbonyl group, the carbonyl group itself being bonded to another atom through its carbon atom.

The term "lower alkyl" represents alkyl groups containing one to six carbons ($C_1$–$C_6$).

The term "halogen" represents fluoro, chloro, bromo, or iodo.

The term "aryl" refers to carbon-based rings which are aromatic. The rings may be isolated, such as phenyl, or fused, such as naphthyl. The ring hydrogens may be substituted with other groups, such as lower alkyl, or halogen.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

The term "heterocycloalkyl" refers to a cycloalkyl ring containing at least one heteroatom, such as N, O, or S, within the ring structure. Examples of heterocycloalkyl rings include tetrahydropyran, pyrrolidine, piperidine, piperazine, tetrahydrothiophene, and morpholine.

The term "heterocycloalkenyl" refers to a cycloalkenyl ring containing at least one heteroatom, such as N, O, or S, within the ring structure. Examples of eterocycloalkenyl rings include dihydropyran, pyrroline, and pyridone.

The HETE derivatives of the present invention are typically derived from arachidonic acid. Certain of the HETE derivatives are known in the art and have been isolated ex vivo as well as prepared biosynthetically and synthetically. Some HETE derivatives are made endogenously by the action of lipoxygenases or other enzymes and subsequent reductions through the actions of endogenous peroxidases. Several lipoxygenases are known to exist and are named for the carbon position which they oxidize. Such enzymes include 5-lipoxygenase, 12-lipoxygenase and 15-lipoxygenase. Other enzymes such as cytochrome P-450 have been observed to catalyze "R-type" HETE oxidized products. Each lipoxygenase catalyzes the addition of a hydroperoxy group at the respective carbon. After hydroperoxidation, which forms such molecules as 5-hydroperoxyeicosatetraenoic acid ("5-HPETE"), 12-HPETE and 15-HPETE, the arachidonate derivatives are reduced to the resulting alcohol by various peroxidases. The resulting molecules include 5-HETE, 12-HETE and 15-HETE.

HETES can be obtained biosynthetically, by in vitro synthesis. Such methods have involved the use of the respective lipoxygenase, $O_2$, arachidonic acid and a suitable reducing agent (See, Graff et al., Activation of Soluble Splenic Cell Guanylate Cyclase by Prostaglandin Endoperoxides and Fatty Acid Hydroperoxides, *Journal of Biological Chemistry*, volume 253, pages 7662–7676 (1978) and Graff, Preparation of 15-L-Hydroperoxy-5,8,11,13-eicosatetraenoic acid (15-HPETE), *Methods in Enzymology*, volume 86, pages 386–392 (1982)). HETEs may also be synthesized by organic synthetic routes such as described in Corey et al., 12-Hydroxy-5,8,14-(Z)-10-(E)- eicosatetraenoic Acid (12-HETE), *The Logic of Chemical Synthesis*, John Wiley and Sons, sections 12.9 and 12.11 (1989). Finally, HETEs are commercially available from various sources including Sigma Chemical Co. (St. Louis, Mo.) and Cayman Chemical (Ann Arbor, Mich.). The level of peroxy compounds in the HETE derivative raw materials that are used to prepare the pharmaceutical formulations of the present invention may have an impact on the HETE derivative's biological activity. Although the precise relationship has not been defined, it is preferable to use HETE derivative raw material supplies containing peroxy compounds at levels no greater than about 0.3 ppm. Methods for determining peroxy levels are known in the art (e.g., European Pharmacopoeia 1997 $3^{rd}$ Ed., Method 2.5.5—Peroxide Value).

It is believed that the use of ethanolic stock solutions of the HETE derivatives in the preparation of the compositions limits the presence of degradation products in the final compositions.

Preferred compounds of the present invention include:

5,8,10,14-Eicosatetraenoic acid, 12-hydroxy-, [12S-(5Z,8Z,10E,14Z)]-("12(S)-HETE");

5,8,11,13-Eicosatetraenoic acid, 15-hydroxy-, [15S-(5Z,8Z,11Z,13E)]-("15(S)-HETE");

The compositions of the present invention comprise one or more HETE derivatives in an amount effective to secrete mucin in the eye and thus eliminate or improve dry eye conditions when administered to the eye. As used herein, the term "pharmaceutically effective amount" refers to an amount of one or more HETE derivatives which improves the dry eye condition in a mammal. Generally, the HETE derivatives will be contained in the compositions in a concentration range of from 0.00001 to about 1 per cent weight/volume ("% w/v"), and preferably 0.00001 to about 0.01% w/v. Compositions comprising 15(S)-HETE in a concentration of from about 0.00001–0.0001% w/v are most preferred.

As stated above, the compositions of the present invention also comprise an effective concentration of ethanol. The inventors of the present invention unexpectedly found that the presence of ethanol in the HETE derivative compositions enhanced the biological efficacy of the HETE derivatives when administered to the eye. As used herein with regard to ethanol, an "amount sufficient to enhance the efficacy of the HETE derivative(s)" refers to a concentration of ethanol that enhances the biological efficacy of the HETE derivative compositions when dosed topically to the eye. In general, the concentration of ethanol necessary for the enhancement of the HETE derivatives is believed to be somewhat proportional to the concentration of the HETE derivative(s) administered. If a relatively high concentration of HETE derivative, e.g., above 0.01% w/v, is administered, the concentration of ethanol in such compositions may be proportionally less than analogous compositions containing lower concentrations of HETE derivatives. In general, however, the ethanol concentration contained in the compositions of the present invention will range from about 0.001–2% w/v. Compositions containing HETE derivative concentrations of about 0.00001–0.01% w/v preferably will contain ethanol in a concentration of about 0.005–0.20% w/v, and most preferably, about 0.02–0.10% w/v.

The HETE derivative compositions will be formulated as solutions, suspensions and other dosage forms for topical administration. Aqueous solutions are generally preferred, based on ease of formulation, biological compatibility (especially in view of the malady to be treated, i.e., dry eye-type disorders), as well as a patient's ability to easily administer such compositions by means of instilling one to two drops of the solutions in the affected eyes. However, the HETE derivative compositions may also be suspensions, viscous or semi-viscous gels, or other types of solid or semi-solid compositions. Suspensions may be preferred for HETE derivatives which are less soluble in water.

Preferably, the compositions of the present invention will also contain a surfactant. Various surfactants useful in topical ophthalmic formulations may be employed. The surfactant(s) may provide additional chemical stabilization of the HETE derivatives and may further provide for the physical stability of the compounds. In other words, the surfactants may aid in preventing chemical degradation of the HETE derivatives and also prevent the compounds from binding to the containers in which their compositions are packaged. As used herein, "an effective concentration of surfactant(s)" refers to a concentration that enhances the chemical and physical stability of HETE derivatives. Examples of surfactants include, but are not limited to: Cremophor® EL, polyoxyl 20 ceto stearyl ether, polyoxyl 40 hydrogenated castor oil, polyoxyl 23 lauryl ether and poloxamer 407 may be used in the compositions. A preferred surfactant is polyoxyl 40 stearate. The concentration of surfactant will vary, will vary, depending on the concentration of the HETE derivative(s) and ethanol included in the formulation. In general, however, the surfactant(s) concentration will be about 0.001 to 2.0% w/v. Preferred compositions of the present invention will contain about 0.1% w/v of polyoxyl 40 stearate.

The pharmaceutical compositions of the present invention may also include various other ingredients, such as tonicity agents, buffers, preservatives, co-solvents and antioxidants.

Various tonicity agents may be employed to adjust the tonicity of the pharmaceutical composition, preferably to that of natural tears. For example, sodium chloride, potassium chloride, magnesium chloride, calcium chloride and/or mannitol may be added to the composition to approximate physiological tonicity. Such an amount of tonicity agent will vary, depending on the particular agent to be added. In general, however, the compositions will have a tonicity agent concentration of about 0.1–1.5% w/v. Preferred pharmaceutical compositions will contain about 0.75% w/v of sodium chloride.

An appropriate buffer system (e.g., sodium phosphate, sodium acetate, sodium citrate, sodium borate or boric acid)

may be added to prevent pH drift under storage conditions. The particular concentration will vary, depending on the agent employed. In general, such a concentration will range from about 0.02 to 2.0% w/v. Preferred compositions will contain about 0.25% w/v of boric acid.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

Antioxidants may be added to compositions of the present invention to protect the HETE salts from oxidation during storage. Examples of such antioxidants include, but are not limited to, vitamin E and analogs thereof, ascorbic acid and derivatives, and butylated hydroxyanisole (BHA).

In a preferred embodiment, the pharmaceutical compositions of the present invention include one or more artificial tear or phospholipid components to provide immediate relief while the HETE salts stimulate natural tear production. In this embodiment, the compositions of the present invention provide a two-pronged approach to the treatment of dry eye. The artificial tear or phospholipid component of the compositions provides immediate, temporary relief of dry eye by lubricating and wetting the eye, and the HETE derivative component of the compositions provides pharmaceutical therapy by stimulating the rebuilding of the patient's natural tears through the stimulation of ocular secretion of mucin. An advantage of compositions according to this embodiment, which provide both immediate, temporary relief as well as long-term dry eye relief, is that they do not need to be administered at high frequency typical of non-therapeutic phospholipid compositions. Instead, the compositions of the present invention may be administered as little as one to two times per day to as much as only about eight to ten times a day, depending on the severity of the dry eye condition.

Another advantage of the compositions containing a HETE salt and an artificial tear or phospholipid component is that the compositions provide ease of use over separate, single therapy compositions. In order for a patient to even attempt to gain both short-term and long-term dry eye relief, the patient would need to juggle two separate composition dosing regimens. With such a two composition regimen, the user is encumbered with handling two separate compositions and following the different dosing regimens. Additionally, due to possible overlap of administration, a user of two separate systems may inadvertently overdose one composition or the other, or effectively over-dilute one composition or the other by concomitant dosing of the two compositions. The present invention would solve such problems by providing a single, multi-therapeutic composition for the treatment of dry eye-type diseases and disorders.

As used herein, "one or more artificial tear or phospholipid components" refers to those components that: (i) lubricate, "wet," approximate the consistency of endogenous tears, or otherwise provide temporary relief of the dry eye symptoms and conditions upon ocular administration; (ii) are safe; and (iii) provide an appropriate delivery vehicle for the topical administration of an effective amount of one or more HETE derivatives. As used herein, "an effective amount of one or more artificial tear or phospholipid components" refers to that amount which lubricates, "wets," approximates the consistency of endogenous tears, or otherwise provides temporary relief of the dry eye symptoms and conditions upon ocular administration. In general, the concentration of the artificial tear or phospholipid components in the compositions of the present invention will range from about 0.01 to about 1.0% w/v (phospholipid component) or 2.0% w/v (non-phospholipid component). Preferred amounts will range from about 0.05 to about 0.1% w/v (phospholipid components) and 0.1–0.5% w/v (non-phospholipid component).

The phospholipid components useful in the compositions of the present invention are any natural or synthetic phospholipid compounds comprising a glycerol-phosphoric acid ester or sphingosine backbone. Examples of phospholipids of the present invention are of formula (IV):

wherein, $X^{21}$ and $X^{22}$ are the same or different and are O, NH(C=O), O(C=O), or a direct bond;

$R^{22}$ is H or $CH=CH(CH_2)_{12}CH_3$;

$X^{21}-R^1$ is OH, or $R^1$ is $C_{12-26}$ substituted or unsubstituted alkyl or alkenyl;

$R^2$ is $C_{12-26}$ substituted or unsubstituted alkyl or alkenyl; and $R^3$ is OH, $OCH_2CH(NH_3^+)COO-$, $OCH_2CH_2NH_3^+$, $OCH_2CH_2N^+(CH_3)_3$, $OCH_2CH(OH)CH_2OH$ and O-inositol.

The phospholipids may be present as racemic or non-racemic compounds. Preferred phospholipids are those wherein $X^{21}-R^1$ and/or $X^{22}-R^2$ comprise fatty acid esters or amides. Natural fatty acids are saturated, monounsaturated or polyunsaturated. Examples of fatty acid residues include, but are not limited to, laurate, myristate, palmitate, palmitoleate, stearate, oleate, linoleate, linolenate, eicosanoate, docosanoate and lignocerate. Preferred phospholipid types are the phosphatidylethanolamines, phosphatidylcholines, phosphatidylserines, phospatidylinositols and sphingomyelins. Examples of specific phospholipids include: 1,2-dipalmitoyl phosphatidyl choline ("DPPC") 1,2-dipalmityl phosphatidyl glycerol ("DPPG"), N-stearyl sphingomyelin, N-palmityl sphingomyelin, N-oleyl sphingomyelin, 1,2-distearoyl phosphatidyl ethanolamine ("DSPE"), 1,2-distearoyl phosphatidyl inositol ("DSPI"), 1-stearoyl-2-pahnitoyl phosphatidyl ethanolamine ("SPPE"), 1-stearoyl-2-palmitoyl phosphatidyl choline ("SPPC"), 1,2-dipalmitoyl phosphatidyl ethanolamine ("DPPE"), 1,2-dioleoyl phophatidyl ethanolamine ("DOPE"), 1,2-dioleoyl phophatidyl serine ("DOPS"), and 1,2-dipalmitoyl phosphatidyl serine ("DPPS"). The most preferred phospholipid carriers are the phosphatidylethanolamines and sphingomyelins. Phospholipids are available from a variety of natural sources and may be synthesized by methods known in the art; see, for example, Tsai et. al., *Biochemistry*, volume 27, page 4619 (1988); and Dennis et. al., *Biochemistry*, volume 32, page 10185 (1993).

Various non-phospholipid artificial tear components are known and are useful in providing lubrication, "wetting,"

approximation of the consistency of endogenous tears, or otherwise providing temporary relief of the dry eye symptoms and conditions upon ocular administration. Such compounds may enhance the viscosity of the composition, and include, but are not limited to: monomeric polyols, such as, glycerol, propylene glycol, ethylene glycol; polymeric polyols, such as, polyethylene glycol, hydroxypropylmethyl cellulose ("HPMC"), carboxy methylcellulose sodium, and hydroxy propylcellulose ("HPC"); hyaluronic acid; chondroitin sulfate; dextrans, such as, dextran 70; water soluble proteins, such as gelatin; and vinyl polymers, such as, polyvinyl alcohol, polyvinylpyrrolidone, povidone and carbomers, such as, carbomer 934P, carbomer 941, carbomer 940, carbomer 974P. In general, the compositions will exhibit a viscosity of 1 to 400 centipoises ("cps"). Preferred compositions will exhibit a viscosity of about 25 cps.

The compositions of the present invention are intended for administration to a mammal suffering from dry eye or symptoms of dry eye. Preferably, the HETE derivatives of the present invention will be administered topically. In general, the doses used for the above described purposes will vary, but will be in an effective amount to alleviate the symptoms of dry eye, increase mucin production in the eye and thus eliminate or improve dry eye conditions. As used herein, the term "therapeutically effective amount" refers to an amount of a composition of the present invention that, when administered to a mammal, improves the dry eye condition of the mammal. Generally, 1–2 drops of the compositions of the present invention will be administered 1–10 times per day, depending on various factors such as the concentration of the HETE derivative(s) in the compositions, the potency of the particular HETE derivatives, as well as the severity of the dry eye disease or disorder to be treated. Preferably, 1–2 drops of the compositions will be administered 1–4 times per day.

As used herein, the term "pharmaceutically acceptable carrier" refers to any formulation which is safe, and provides the appropriate delivery of an effective amount of at least one HETE derivative of the present invention and an effective amount of ethanol.

The following Examples 1—describe preferred compositions of the present invention. Variations of the exemplified compositions may also be prepared, e.g., substituting a HETE derivative of formula (I) or (II) for the compound of formula (III), modifying the concentration of the HETE derivative to between about 0.00001 to 1% w/v, varying the concentrations of the other components present, and modifying the pH (e.g., between about 6–8).

EXAMPLE 1

| Ingredient | Amount (% w/v) |
| --- | --- |
| Compound of Formula (III) | 0.000034 |
| Ethanol | 0.0505 |
| Polyoxyl 40 Stearate | 0.1 |
| Boric Acid | 0.25 |
| Sodium Chloride | 0.75 |
| Disodium Edetate | 0.01 |
| Polyquaternium-1 | 0.001 |
| NaOH/HCl | q.s., pH = 7.5 |
| Purified Water | q.s. 100% |

The above composition is prepared by the following method. The batch quantities of polyoxyl 40 stearate, boric acid, sodium chloride, disodium edetate, and polyquaternium-1 are weighed and dissolved by stirring in 90% of the batch quantity of purified water. The pH is adjusted to 7.5±0.1 with NaOH and/or HCl. Under yellow light or reduced lighting, the batch quantity of the chosen compound of formula (III) as a stock solution in ethanol and the additional quantity of ethanol necessary for the batch are measured and added. Purified water is added to q.s. to 100%. The mixture is stirred for five minutes to homogenize and then filtered through a sterilizing filter membrane into a sterile recipient.

Preferably, the above process is performed using glass, plastic or other non-metallic containers or containers lined with such materials.

EXAMPLE 2

| Ingredient | Amount (% w/v) |
| --- | --- |
| Compound of Formula (III) | 0.000034 |
| Ethanol | 0.0505 |
| Boric Acid | 0.25 |
| Sodium Chloride | 0.75 |
| Disodium Edetate | 0.01 |
| Polyquaternium-1 | 0.001 |
| NaOH/HCl | q.s., pH = 7.5 |
| Purified Water | q.s. 100% |

The above formulation may be made by a method similar to the method described in Example 1.

EXAMPLE 3

| Ingredient | Amount (% w/v) |
| --- | --- |
| Compound of Formula (III) | 0.000034 |
| Polyoxyl 40 Stearate | 0.1 |
| Ethanol | 0.0505 |
| Boric Acid | 0.25 |
| Sodium Chloride | 0.75 |
| NaOH/HCl | q.s., pH = 7.5 |
| Purified Water | q.s. 100% |

The above formulation may be made by a method similar to the method described in Example 1.

EXAMPLE 4

A composition of the present invention (Example 1, with the compound of formula (III) being 15(S)-HETE) was compared to an analogous composition without ethanol, an analogous composition without 15(S)-HETE, and analogous compositions with approximately one-half, one-tenth, and twice the amount of ethanol, respectively, in an in vivo desiccation model of dry eye.

Briefly, the assay was performed by first anesthetizing the animals with ketamine/xylazine/glycopyrrolate. The O.S. eye was lubricated with DuraTears® and remained taped shut throughout the experiment. The O.D. eye was then dosed with 50 μL of test composition (Example 1) or 50 μL of the same composition without ethanol and the eye taped shut for 10 minutes. The tape was then removed, the eyelids opened and a speculum was inserted into the eye. The eye was held open with the speculum for a period of 4 hours. During this time, the animals were monitored every 15 minutes and supplemental injections of ketamine/xylazine (at half the initial dose/injection) were administered as needed to maintain anesthesia. At the end of the 4-hour period, 2 sutures were placed in the upper eyelid and 1 suture was placed in the lower eyelid. A corneal/conjunctival cup was formed by using the sutures to lift the eyelids upward and the sutures taped to a stand. 1 mL methylene blue (1% solution in water) was added to the conjunctival cup and the cornea was stained with the solution for 5 minutes. The eye was then washed with 200 mL of a balanced salt solution. Corneal thickness was determined by non-invasive pachymetry. Three readings were taken for each animal. Corneal staining score was obtained by visualizing the cornea with a slit-lamp and determining the percentage of the cornea that was stained with methylene blue. A photograph was taken using the slit-lamp machine. The rabbit was then euthanized immediately by intravenous injection of Sleepaway® solution and the eye was excised. The cornea was isolated and an 8 mm punch of the central cornea collected. This corneal punch was placed in a small glass vial containing 2 mL acetone/saturated sodium sulfate (7:3, vol/vol). Absorbance of the extracted solution was measured at 660 nm with a spectrophotometer.

The naïve control animals were anesthetized with ketamine/xylazine/glycopyrrolate and the O.S. eye lubricated and taped shut. Sutures were immediately placed in the O.D. eyelids. The corneal cup was formed and the cornea was stained with methylene blue, washed with a balanced salt solution and collected, as described above. The data were converted to "percent protection" by subtracting from 1, the quotient of the test sample absorbances divided by the average of control sample absorbance, and multiplying by 100. The results are contained in Table 1 and illustrated in FIGS. 1 and 2:

TABLE 1

Figure 1:
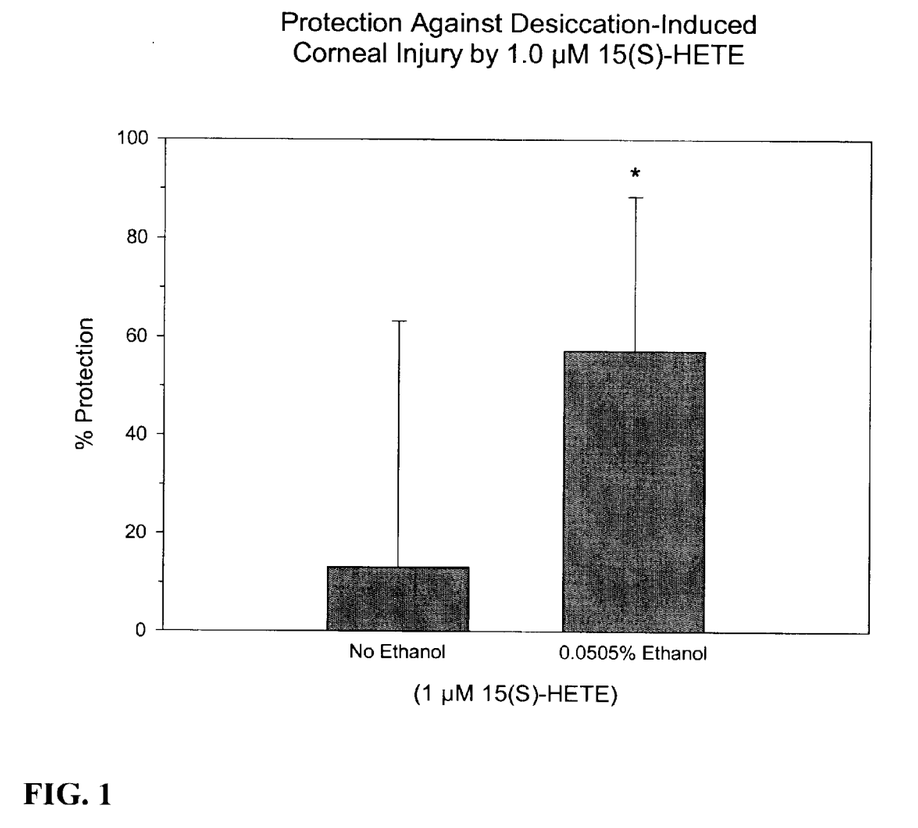
FIG. 1 is a graph illustrating the improved dry eye efficacy of a composition comprising 15(S)-HETE and ethanol versus an analogous composition containing no ethanol in an in vivo dry eye model.
Figure 2:
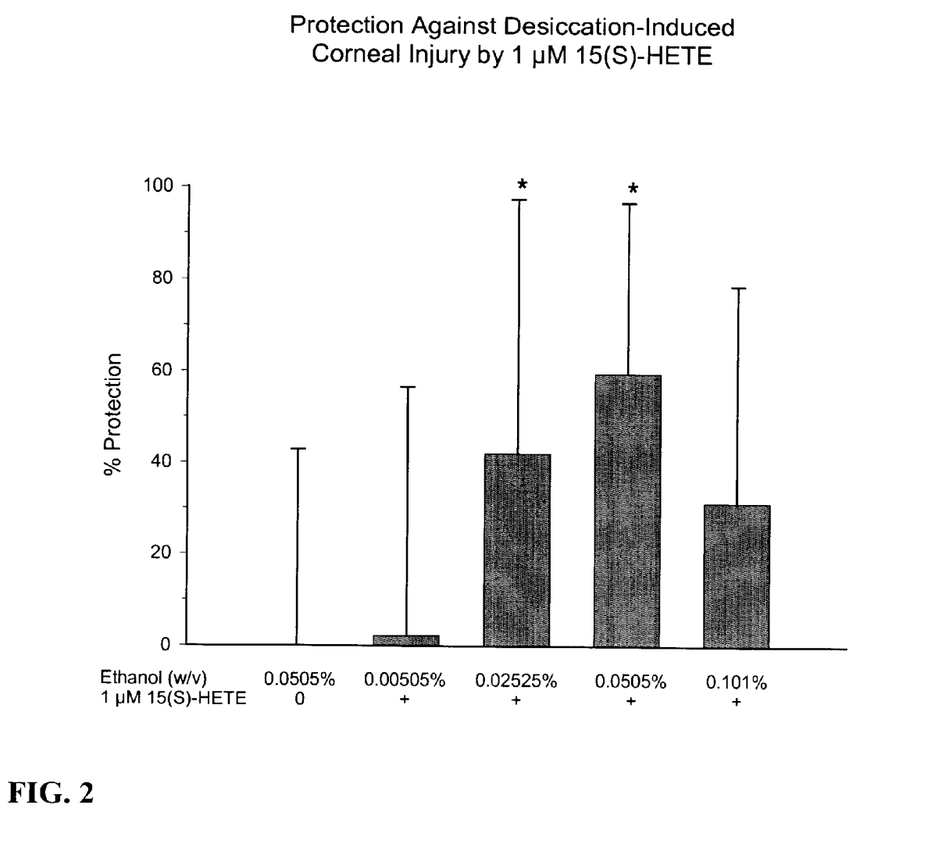
FIG. 2 is a graph illustrating the improved dry eye efficacy of compositions comprising 15(S)-HETE and varying concentrations of ethanol versus a composition containing no 15(S)-HETE in an in vivo dry eye model.

| Composition | | |
|---|---|---|
| Ethanol % (w/v) | 15(S)-HETE | % Protection |
| 0.0 | 1 μM | 13 |
| 0.0505 | 0 | 0 |
| 0.00505 | 1 μM | 2 |
| 0.0252* | 1 μM | 42 |
| 0.0505* | 1 μM | 60 |
| 0.101 | 1 μM | 31 |

*p < 0.05 versus control. Note: 1 μM corresponds to 0.000034% w/v

The above results demonstrate the effects of ethanol in combination with a HETE derivative on the protection against corneal injury induced by dry eye conditions.

The following Examples 5–10 (phospholipid compositions) and 11–19 (non-phospholipid artificial tear component compositions) illustrate specific compositions of the present invention.

EXAMPLE 5

| Ingredient | Amount (% w/v) |
|---|---|
| Compound of Formula (III) | 0.000034 |
| Ethanol | 0.0505 |
| DPPC | 0.05 |
| DPPE | 0.05 |
| Polyoxyl 40 stearate | 0.1 |
| Sodium Chloride | 0.8 |
| Potassium Chloride | 0.12 |
| Dibasic Sodium Phosphate | 0.025 |
| Disodium EDTA | 0.01 |
| Polyquaternium-1 | 0.001 + 10% excess |
| Purified Water | Qs |
| NaOH/HCl | qs to pH 6–8 |

The above composition is prepared by the following method. The batch quantities of DPPC, DPPG, sodium chloride, potassium chloride, dibasic sodium phosphate, disodium EDTA, polyquaternium-1, are weighed and dissolved by stirring in 90% of the batch quantity of purified water. The pH is adjusted to 7.5±0.1 with NaOH and/or HCl. Under yellow light or reduced lighting, the batch quantity of the chosen compound of formula (m) as a stock solution in ethanol and the additional quantity of ethanol necessary for the batch are measured and added. Purified water is added to q.s. to 100%. The mixture is stirred for five minutes to homogenize and then filtered through a sterilizing filter membrane into a sterile recipient.

Preferably, the above process is performed using glass, plastic or other non-metallic containers or containers lined with such materials.

The formulations of Examples 6–10 may be made by a method similar to that described in Example 5.

EXAMPLE 6

| Ingredient | Amount (% w/v) |
|---|---|
| Compound of Formula (III) | 0.000034 |
| Ethanol | 0.0505 |
| N-Stearyl Sphingomeylin | 0.1 |
| Sodium Chloride | 0.8 |
| Potassium Chloride | 0.12 |
| Dibasic Sodium Phosphate | 0.025 |
| Disodium EDTA | 0.01 |
| Polyquaternium-1 | 0.001 + 10% excess |
| Purified Water | Qs |
| NaOH/HCl | qs to pH 6–8 |

EXAMPLE 7

| Ingredient | Amount (% w/v) |
|---|---|
| HETE derivative | 0.00001–0.01 |
| Ethanol | 0.005–0.20 |
| DPPE | 0.05 |
| DSPE | 1.0 |
| Sodium Chloride | 0.8 |
| Potassium Chloride | 0.12 |
| Dibasic Sodium Phosphate | 0.025 |
| Disodium EDTA | 0.01 |
| Polyquaternium-1 | 0.001 + 10% excess |
| Purified Water | Qs |
| NaOH/HCl | qs to pH 6–8 |

EXAMPLE 8

| Ingredient | Amount (% w/v) |
|---|---|
| HETE derivative | 0.00001–0.01 |
| N-oleyl Sphingomyelin | 0.08 |
| DPPE | 0.04 |
| Sodium Chloride | 0.8 |
| Potassium Chloride | 0.12 |
| Dibasic Sodium Phosphate | 0.025 |
| Polyquaternium-1 | 0.001 + 10% excess |
| Purified Water | Qs |
| NaOH/HCl | qs to pH 6–8 |

EXAMPLE 9

| Ingredient | Amount (% w/v) |
| --- | --- |
| HETE derivative | 0.00001–0.01 |
| DOPS | 0.1 |
| Sodium Chloride | 0.8 |
| Dibasic Sodium Phosphate | 0.025 |
| Disodium EDTA | 0.01 |
| Polyquaternium-1 | 0.001 + 10% excess |
| NaOH/HCl | qs to pH 6–8 |

EXAMPLE 10

| Ingredient | Amount (% w/v) |
| --- | --- |
| HETE derivative | 0.00001–0.01 |
| N-palmityl Sphingomyelin | 0.1 |
| Sodium Chloride | 0.8 |
| Dibasic Sodium Phosphate | 0.025 |
| Disodium EDTA | 0.01 |
| Polyquaternium-1 | 0.001 + 10% excess |
| NaOH/HCl | qs to pH 6–8 |

EXAMPLE 11

| Ingredient | Amount (% w/v) |
| --- | --- |
| 15(S)-HETE Sodium Salt | 0.000034 |
| Ethanol | 0.0505 |
| Polyoxyl 40 Stearate | 0.1 |
| HPMC | 0.3 |
| Dextran 70 | 0.1 |
| Benzalkonium Chloride | 0.001 + 10% excess |
| Sodium Chloride | 0.77 |
| Potassium Chloride | 0.12 |
| Disodium EDTA | 0.05 |
| Purified Water | Qs |
| NaOH/HCl | pH 6–8 |

The above composition is prepared by the following method. The batch quantities of HPMC, dextran 70, benzalkonium chloride, sodium chloride, potassium chloride and disodium EDTA are weighed and dissolved by stirring in 90% of the batch quantity of purified water. The pH is adjusted to 7.5±0.1 with NaOH and/or HCl. Under yellow light or reduced lighting, the batch quantity of the chosen compound of formula (III) as a stock solution in ethanol and the additional quantity of ethanol necessary for the batch are measured and added. Purified water is added to q.s. to 100%. The mixture is stirred for five minutes to homogenize and then filtered through a sterilizing filter membrane into a sterile recipient.

Preferably, the above process is performed using glass, plastic or other non-metallic containers or containers lined with such materials.

The formulations of Examples 12–19 may be made by a method similar to that described in Example 11.

EXAMPLE 12

| Ingredient | Amount (% w/v) |
| --- | --- |
| Compound of Formula (III) | 0.000034 |
| Ethanol | 0.0505 |
| Polyoxyl 40 Stearate | 0.1 |
| HPMC | 0.3 |
| Dextran 70 | 0.1 |
| Sodium Chloride | 0.8 |
| Potassium Chloride | 0.12 |
| Dibasic Sodium Phosphate | 0.025 |
| Disodium EDTA | 0.01 |
| Polyquaternium-1 | 0.001 + 10% excess |
| Purified Water | Qs |
| NaOH/HCl | qs to pH 6–8 |

EXAMPLE 13

| Ingredient | Amount (% w/v) |
| --- | --- |
| Compound of Formula (III) | 0.000034 |
| Ethanol | 0.0505 |
| Polyoxyl 40 Stearate | 0.1 |
| HPMC | 0.3 |
| Dextran 70 | 0.1 |
| Sodium Chloride | 0.52 |
| Potassium Chloride | 0.12 |
| Dibasic Sodium Phosphate | 0.35 |
| Purified Water | Qs |
| NaOH/HCL | qs to pH 6–8 |

EXAMPLE 14

| Ingredient | Amount (% w/v) |
| --- | --- |
| Compound of Formula (III) | 0.000034 |
| Polyoxyl 40 Stearate | 0.1 |
| HPMC | 0.3 |
| Dextran 70 | 0.1 |
| Sodium Chloride | 0.66 |
| Potassium Chloride | 0.13 |
| Calcium Chloride | 0.0053 |
| Magnesium Chloride | 0.0065 |
| Zinc Chloride | 0.00015 |
| Sodium Bicarbonate | 0.12 |
| Carbon Dioxide/NaOH/HCl | qs to pH 6–8 |
| Purified Water | Qs |

EXAMPLE 15

| Ingredient | Amount (% w/v) |
| --- | --- |
| Compound of Formula (III) | 0.000034 |
| Ethanol | 0.0505 |
| Polyoxyl 40 Stearate | 0.1 |
| HPMC | 0.3 |
| Dextran 70 | 0.1 |
| Sodium Chloride | 0.66 |
| Potassium Chloride | 0.13 |
| Sodium Bicarbonate | 0.12 |
| Carbon Dioxide/NaOH/HCl | qs to pH 6–8 |
| Purified Water | Qs |

EXAMPLE 16

| Ingredient | Amount (% w/v) |
| --- | --- |
| Compound of Formula (III) | 0.000034 |
| Polyoxyl 40 Stearate | 0.1 |
| Carbomer 934P | 0.3 |
| Mannitol | 4.5 |
| Purified Water | Qs |
| NaOH/HCl | qs to pH 6–8 |

EXAMPLE 17

| Ingredient | Amount (% w/v) |
| --- | --- |
| Compound of Formula (III) | 0.000034 |
| Polyoxyl 40 Stearate | 0.1 |
| Carbomer 934P | 0.3 |
| Mannitol | 4.5 |
| Benzalkonium Chloride | 0.008 + 5% excess |
| Purified Water | Qs |
| NaOH/HCl | qs to pH 6–8 |

EXAMPLE 18

| Ingredient | Amount (% w/v) |
| --- | --- |
| Compound of Formula (III) | 0.000034 |
| HPMC | 0.5 |
| Carbomer 934P | 0.175 |
| Mannitol | 4.5 |
| Purified Water | Qs |
| NaOH/HCl | qs to pH 6–8 |

EXAMPLE 19

| Ingredient | Amount (% w/v) |
| --- | --- |
| Compound of Formula (III) | 0.000034 |
| Ethanol | 0.0505 |
| Polyoxyl 40 Stearate | 0.1 |
| HPMC | 1.0 |
| Dextran 70 | 0.1 |
| Sodium Chloride | 0.66 |
| Potassium Chloride | 0.13 |
| Calcium Chloride | 0.0053 |
| Magnesium Chloride | 0.0065 |
| Zinc Chloride | 0.00015 |
| Sodium Bicarbonate | 0.12 |
| Carbon Dioxide/NaOH/HCl | qs to pH 6–8 |
| Purified Water | Qs |

The invention in its broader aspects is not limited to the specific details shown and described above. Departures may be made from such details within the scope of the accompanying claims without departing from the principles of the invention and without sacrificing its advantages.

What is claimed is:

1. A composition for the treatment of dry eye and other disorders requiring the wetting of the eye comprising a pharmaceutically acceptable carrier, a pharmaceutically effective amount of one or more HETE derivatives according to formulas (I), (II) or (III), and ethanol in an amount sufficient to enhance the efficacy of the HETE derivative(s):

(I)

(II)

(III)

wherein:

X is OR or NHR;

R is H, substituted or unsubstituted alkyl, cycloalkyl, (cycloalkyl)alkyl, aryl, arylalkyl, wherein the substitution is made with a moiety selected from the group consisting of: alkyl, halogen, hydroxy and functionally modified hydroxy; and Y is wherein R" is H or OR" is a functionally modified hydroxy group.

2. The composition of claim 1, wherein the HETE derivative is selected from the group consisting of: 5(S)-HETE, 5(R)-HETE, 12(S)-HETE, 12(R)-HETE, 15(S)-HETE, 15(R)-HETE and racemic and non-racemic mixtures thereof.

3. The composition of claim 1, wherein the HETE derivative is 15(S)-HETE.

4. The composition of claim 3, wherein the HETE derivative is contained in the composition in a concentration of between 0.00001 to 0.01% w/v.

5. The composition of claim 1, wherein the composition further comprises a surfactant.

6. The composition of claim 1, wherein the ethanol concentration is between 0.001–2% w/v.

7. The composition of claim 4, wherein the ethanol concentration is between 0.005–0.20% w/v.

8. The composition of claim 1 further comprising one or more artificial tear or phospholipid components.

9. The composition of claim 8 wherein the composition comprises a phospholipid selected from the group consisting of are selected from the group consisting of phosphatidylethanolamines, phosphatidylcholines, phosphatidylserines, phospatidylinositols and sphingomyelins.

10. The composition of claim 8 wherein the composition comprises a phospholipid of the formula:

(IV)

wherein, $X^{21}$ and $X^{22}$ are the same or different and are O, NH(C=O), O(C=O), or a direct bond;

$R^{22}$ is H or CH=CH(CH$_2$)$_{12}$CH$_3$;

$X^{21}$—$R^1$ is OH, or $R^1$ is C$_{12-26}$ substituted or unsubstituted alkyl or alkenyl;

$R^2$ is C$_{12-26}$ substituted or unsubstituted alkyl or alkenyl; and $R^3$ is OH, OCH$_2$CH(NH$_3^+$)COO$^-$, OCH$_2$CH$_2$NH$_3^+$, OCH$_2$CH$_2$N$^+$(CH$_3$)$_3$, OCH$_2$CH(OH)CH$_2$OH and O-inositol.

11. The composition of claim 10, wherein the phospholipid is selected from the group consisting of: DPPC, DPPG, DSPI, SPPC, DPPE, DOPS, DSPE, SPPE, DOPE, DPPS, N-stearyl sphingomyelin, N-palmityl sphingomyelin and N-oleyl sphingomyelin.

12. The composition of claim 8 wherein the composition comprises an artificial tear component selected from the group consisting of monomeric polyols; polymeric polyols; hyaluronic acid; chondroitin sulfate; dextrans; water-soluble proteins; and vinyl polymers.

13. The composition of claim 12 wherein the artificial tear component is selected from the group consisting of glycerol; propylene glycol; ethylene glycol; polyethylene glycol; hydroxypropylmethyl cellulose; carboxy methylcellulose sodium; hydroxy propylcellulose; hyaluronic acid; chondroitin sulfate; dextran 70; gelatin; polyvinyl alcohol; polyvinylpyrrolidone; povidone; carbomer 934P; carbomer 941; carbomer 940; and carbomer 974P.

14. The composition of claim 1, wherein the composition further comprises one or more ingredients selected from the group consisting of surfactants, tonicity agents, buffers, preservatives, co-solvents and anti-oxidants.

15. A method for the treatment of dry eye and other disorders requiring the wetting of the eye comprising administering to a mammal a composition comprising a pharmaceutically effective amount of one or more HETE derivatives according to formulas (I), (II) or (III), and ethanol in an amount sufficient to enhance the efficacy of the HETE derivative(s):

(I)

wherein:

X is OR or NHR;

R is H, substituted or unsubstituted alkyl, cycloalkyl, (cycloalkyl)alkyl, aryl, arylalkyl, wherein the substitution is made with a moiety selected from the group consisting of: alkyl, halogen, hydroxy and functionally modified hydroxy; and Y is wherein R" is H or OR" is a functionally modified hydroxy group.

16. The method of claim 15, wherein the HETE derivative is selected from the group consisting of: 5(S)-HETE, 5(R)-HETE, 12(S)-HETE, 12(R)-HETE, 15(S)-HETE, 15(R)-HETE and racemic and non-racemic mixtures thereof.

17. The method of claim 16, wherein the HETE derivative is 15(S)-HETE.

18. The method of claim 15, wherein the HETE derivative is contained in the composition in a concentration of between 0.00001 to 0.01% w/v.

19. The method of claim 15, wherein the composition further comprises a surfactant.

20. The method of claim 15, wherein the ethanol concentration in the composition is between 0.001–2% w/v.

21. The method of claim 20, wherein the ethanol concentration in the composition is between 0.005–0.20% w/v.

22. The method of claim 15 wherein the dry eye and other disorders requiring wetting of the eye is symptoms of dry eye associated with refractive surgery.

* * * * *